United States Patent [19]

Youngman

[11] Patent Number: 4,494,399
[45] Date of Patent: Jan. 22, 1985

[54] TOXIC GAS DETECTION SYSTEM CALIBRATOR

[75] Inventor: George Youngman, Park Ridge, N.J.

[73] Assignee: Becton, Dickinson & Co., Paramus, N.J.

[21] Appl. No.: 440,773

[22] Filed: Nov. 10, 1982

[51] Int. Cl.³ .................................................. G01N 27/26
[52] U.S. Cl. ........................................ 73/1 G; 204/406
[58] Field of Search ..................... 73/1 G, 1 R, 900; 330/108; 204/406, 424, 431

[56] References Cited

U.S. PATENT DOCUMENTS

| | | | |
|---|---|---|---|
| 3,776,832 | 12/1973 | Oswin et al. | 204/411 |
| 3,824,167 | 7/1974 | Oswin et al. | 204/411 |
| 3,992,267 | 11/1976 | Oswin et al. | 204/1 T |
| 4,001,103 | 1/1977 | Blurton et al. | 204/411 |
| 4,094,186 | 6/1978 | Wessel | 73/1 G |
| 4,150,495 | 4/1979 | Stern | 73/1 G X |
| 4,151,738 | 5/1979 | Hyer et al. | 73/1 G |
| 4,399,684 | 8/1983 | Advani et al. | 73/1 G |

Primary Examiner—Stephen A. Kreitman
Assistant Examiner—Tom Noland
Attorney, Agent, or Firm—Larson and Taylor

[57] ABSTRACT

An arrangement is provided for the simplified and rapid recalibration of electrochemical toxic gas detectors. Periodically, a single untrained operator may temporarily operate the system of the invention for adjusting the "span" and "zero" settings on the sensor, make two adjustments until he obtains a signal, such as a light signal, in order to obtain recalibration. The arrangement allows the use of untrained personnel to make otherwise technical adjustments in remote regions where gas detectors may be utilized. The system of the invention may be located at the sensing head of the toxic gas sensor or at the controller thereof.

6 Claims, 3 Drawing Figures

TOXIC GAS DETECTION SYSTEM CALIBRATOR

BACKGROUND AND STATEMENT OF THE INVENTION

This invention relates generally to electrochemical gas sensors for sensing gases which may be toxic to human beings in a specific area such as a mine shaft, for example. More particularly, this invention relates to a simplified calibration system for recalibrating such toxic gas sensors periodically in order to maintain them at a proper sensing level on a continuous basis. The invention may be utilized for recalibrating electrochemical sensors such as those taught and claimed in U.S. Pat. Nos. 3,776,832, 3,824,167 and 3,992,267, all by Harry G. Oswin et al and U.S. Pat. No. 4,001,103 to Blurton et al. Such sensors may be placed as noted above, in areas such as mine shafts or garages for detecting gases present in the ambient which may be dangerous to individuals in the area being protected by the sensor. Such gases include, for example, carbon monoxide, nitric oxide, nitrogen dioxide, and hydrazine.

Such gas sensors must be adjusted periodically because the sensor output changes with time, and two adjustments must be made, the "zero" calibration and the "span" calibration. The "zero" calibration consists of applying clean air to the sensing head of the toxic gas sensor in order to obtain an exact "zero" reading on the sensor. The "span" calibration consists of applying a gas of known concentration, and adjusting the gain of the resulting signal so that the system controller is displaying the correct gas concentration when it is actually sensed.

As will be appreciated, many such sensors are placed in remote areas. Since they must be periodically adjusted, in the past it has been necessary for two operators to go to the remote areas periodically for making the recalibration adjustments. As will be appreciated, the use of experienced technicians for making periodic adjustments in remote areas can be expensive.

With this invention, by contrast, an inexperienced person routinely present in the area being monitored may carry out the adjustments in a simplified manner simply by going to the arrangement of the invention here and making two adjustments. First by closing off the sensing head to ambient, so that the sensor is not exposed to the ambient for picking up any toxic gas, the zero adjustment may be made. At that point, the inexperienced operator may simply turn a knob until a light signal comes on indicating that a proper adjustment has been made. With the "span" adjustment, he simply connects a source of gas of known concentration supplied to him, and makes a second adjustment until a light signal comes on. It is not necessary for the inexperienced operator to have any training other than to note the appearance of the light signal. The arrangement, in accordance herewith, is such that if an over adjustment is made the light signal goes off. Thus, the arrangement provides for an upper and lower limit to adjust to a proper range of signal for both the "zero" and "span" adjustments.

Other objects and advantages of this invention will be apparent from the following description, the accompanying drawings, and the appended claims.

DETAILED DESCRIPTION OF THE INVENTION

Figure 1:
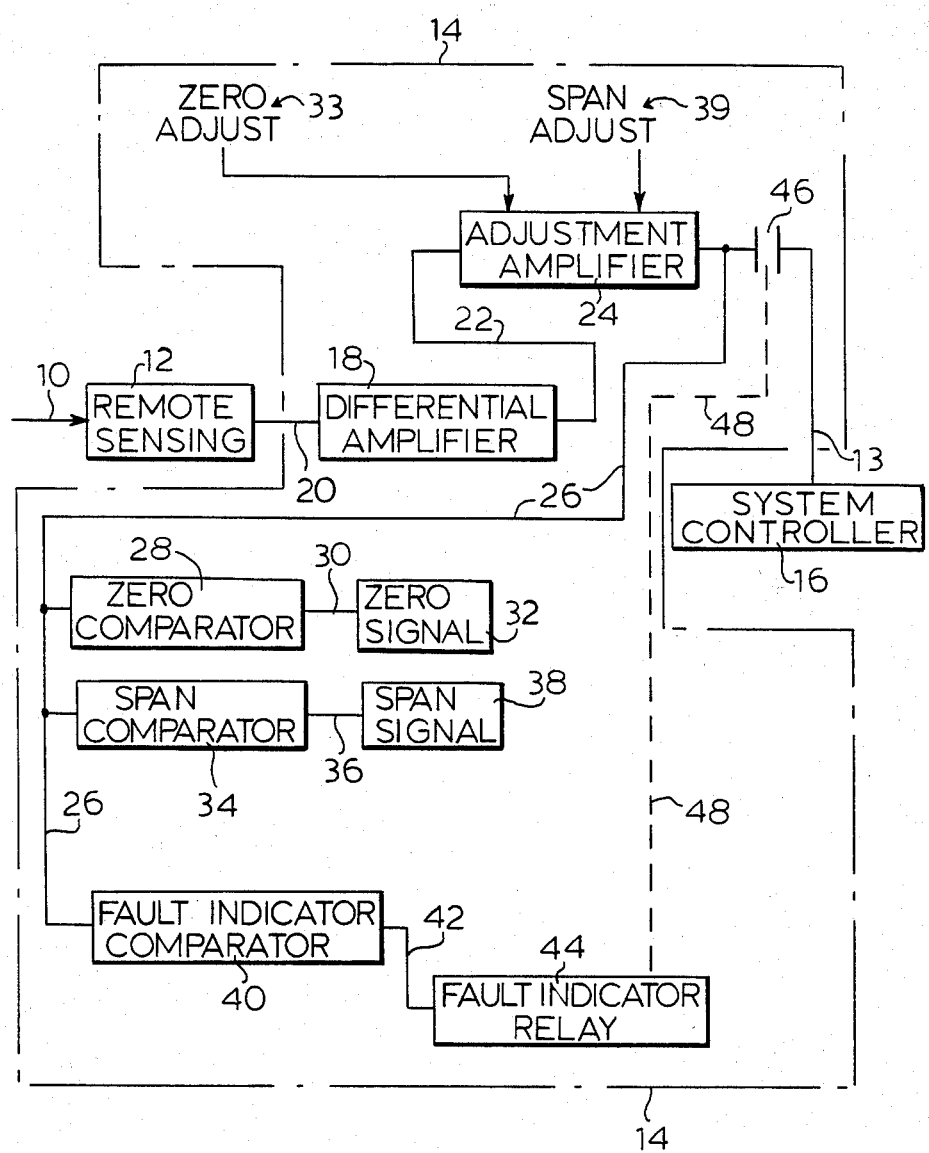
FIG. 1 is a block diagram of a calibrator illustrating the invention.

Referring to the drawings in which like reference characters refer to like parts throughout the several views thereof FIG. 1 shows a remote sensing head 12 receiving a source of ambient gas 10. Remote sensing head 12 is connected through line 20 to the remote calibrator system of the invention. The remote calibrator system is housed within a housing 14 and is, in turn, connected through line 13 to a toxic gas detection system controller 16. In FIG. 1, line 20 which carries a dual wire signal, as will be discussed below, leads to a differential amplifier 18. Amplifier 18 converts the floating signal to a single ended signal 22 which leads to an adjustment amplifier 24. Adjustment amplifier 24 is adjusted by a "span" adjustment 39 and a "zero" adjustment 33.

That is, as discussed previously, the toxic gas sensor system must be calibrated periodically in order to adjust for any changes in the system over a period of time. To do so, the "zero" adjust arrangement is made to bring the system to a "zero" signal when receiving no gas. This is done by blocking line 10 to remote sensing head 12, allowing the system to come to a stable condition, and then adjusting the "zero" adjust 33 in order to impart to the adjustment amplifier this adjustment. Thereafter, line 10 is fed with a span gas which is a gas of known concentration of a toxic gas being sensed. Again, the operator waits for the system to come to a stable condition and adjusts the "span" adjust 39.

The remote calibrator arrangement of the invention includes a "zero" comparator 28, a "span" comparator 34 and a fault indicator comparator 40. All three comparators are connected by line 26 to adjustment amplifier 24. Thus, the operator, when blocking line 10 to the remote sensing head, makes an adjustment in the "zero" adjust 33 which adjustment is reflected at "zero" comparator 28. When the "zero" adjust is a correct one a "zero" signal 32, connected to the "zero" comparator through line 30 is activated indicating to the operator that he has made the proper "zero" adjust. This is an automatic built-in arrangement so that the operator merely has to block line 10, allow the system to come to a stable condition from this block change and then adjust the signal until an indication is made that he has made the correct adjustment.

The same procedure applies with "span" comparator 34 which is connected through line 36 to a "span" signal 38. A "span" gas is connected to line 10 going to the remote sensing head 12. After allowing the system to become stable, the operator adjusts the "span" adjust 39 until a signal is shown at 38.

The fault indicator comparator 40 is arranged to keep the fault indicator relay 44, connected to comparator 40 through line 42, energized. If the output signal goes above a preset threshhold signal, fault indicator relay 44 deenergizes through line 48 causing the output in line 13 to signal controller 16 to break at 46.

Figure 2A:
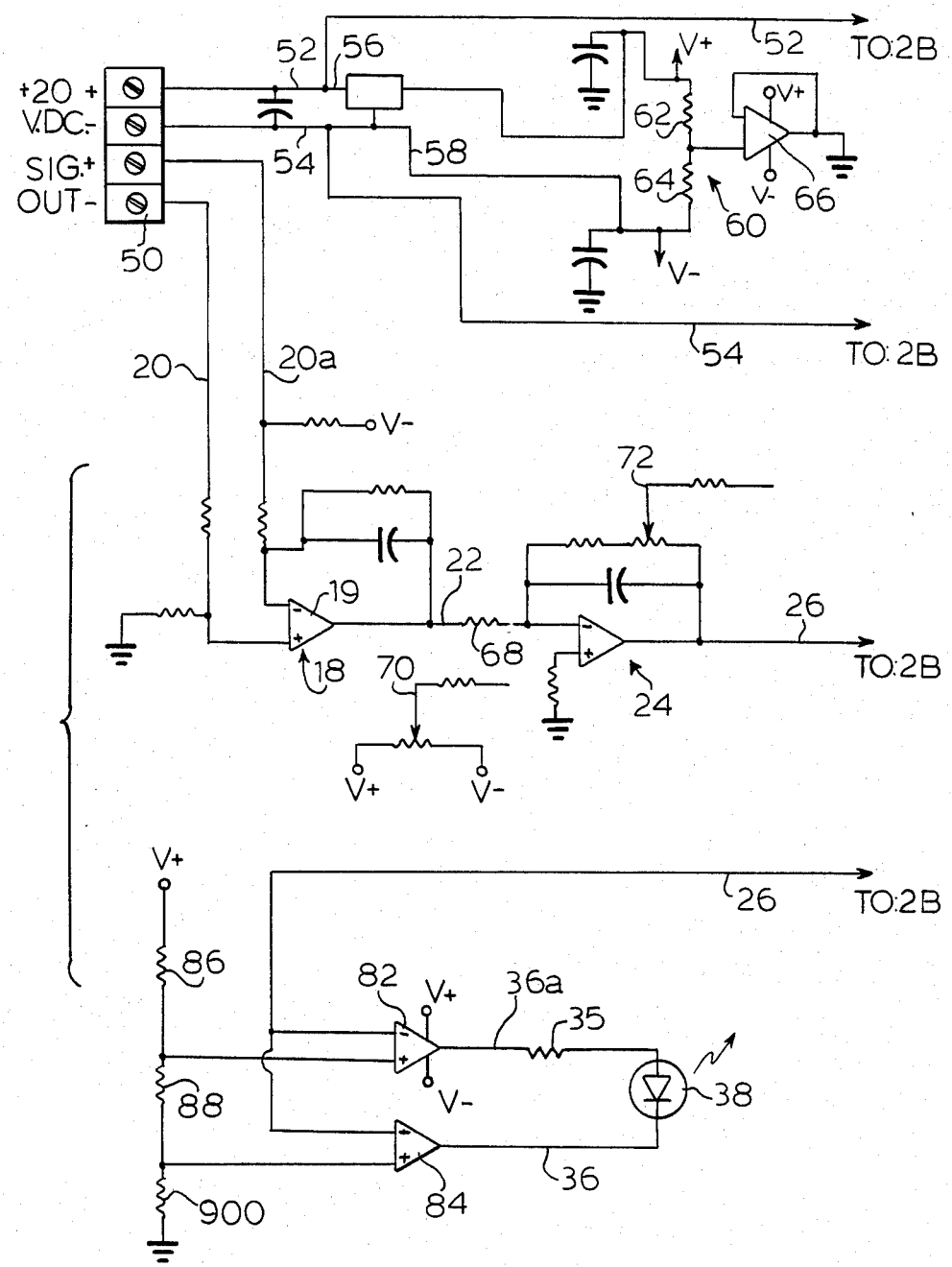
FIGS. 2A and 2B are diagrammatic or schematic indications of the electrical circuit of a toxic gas detection system calibrator illustrating the invention.
Figure 2B:
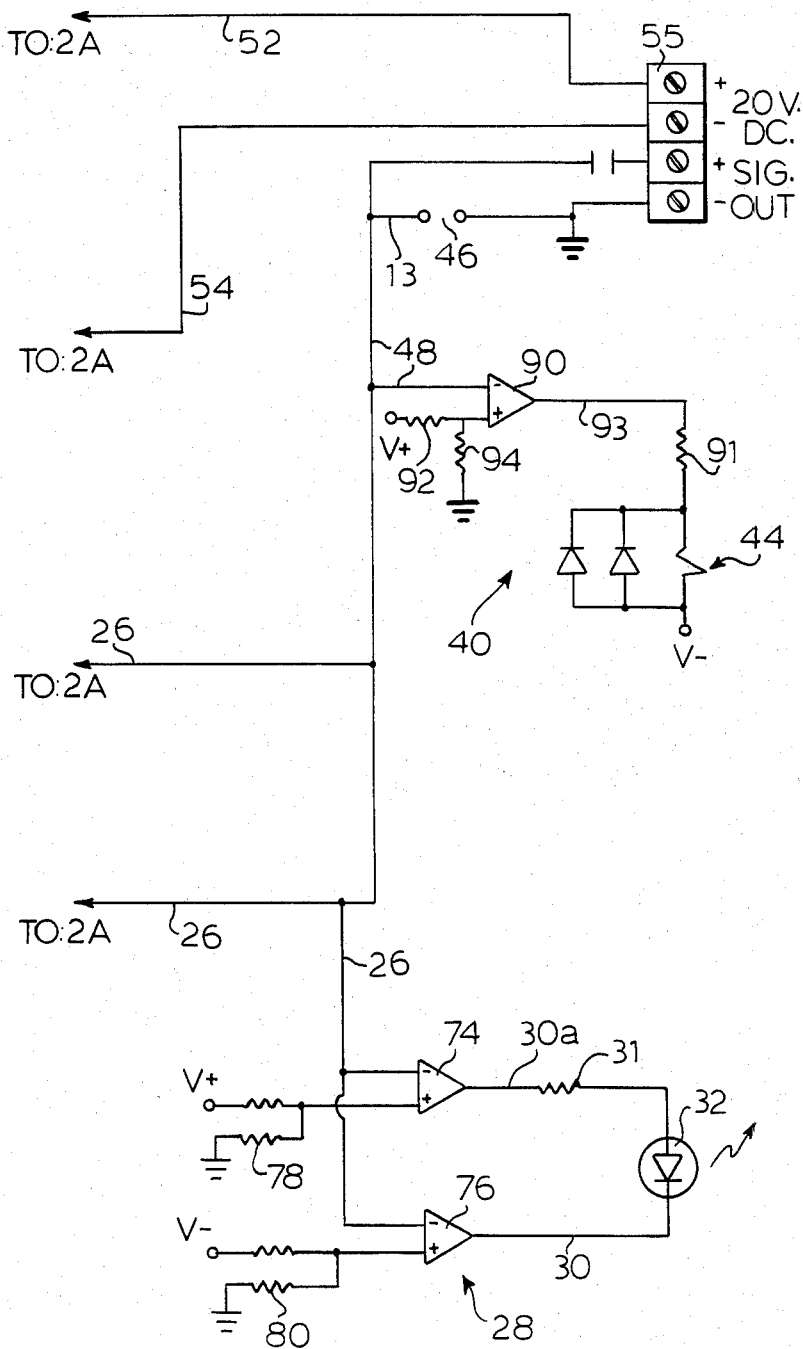

Referring now to the detailed schematic shown in FIGS. 2A and 2B, input terminals collectively denoted 50 are shown (FIG. 2A) which are connected to the sensing head. Two of these terminals are connected by lines 52, 54 to corresponding terminals of the output connector 55. Lines 52, 54 are connected by lines 56, 58 to the circuitry 60 including resistors 62, 64 and operational amplifier 66 for energizing the circuitry for the calibrator of the invention. The other two terminals of the input terminals at connector 50 are connected through the dual signal lines 20, 20a to operational amplifier 19 in the differential amplifier circuitry 18 which serves to convert the dual signal from lines 20, 20a to a single signal line 22 leading through resistor 68 to adjustment amplifier 24. Adjustment amplifier 24 includes a "zero" adjustment resistor 70 and a "span" adjustment resistor 72.

As discussed above, adjustment amplifier 24 is connected through line 26 to a "zero" comparator circuitry 28 consisting of operational amplifiers 74, 76. When the gas leading to remote sensing head 12 is blocked, and the system becomes stable, the operator adjusts resistor 70 so that the output signal of amplifiers 74, 76 is within a predetermined band around zero volts, as determined by resistors 78, 80 connected to amplifiers 74, 76, respectively. When this happens, the comparator 28 trips and turns on signal 32, which may be, for example, a light emitting diode. If the operator adjusts too far above the "zero" signal, the light or other signal 32 goes off again until the operator returns to the proper range as established by resistors 78, 80.

The signal adjustment amplifier 24 is also connected to the "span" comparator 34 consisting of operational amplifiers 82, 84 respectively. These amplifiers are, in turn, connected through lines 36a, 36 respectively to a "span" signal 38, which also may be a light emitting diode signal. As will be appreciated, signals 32, 38 may be of different colors to differentiate between the "zero" and the "span" comparisons. Signal 32 is also connected to its associated amplifier 74, 76 through lines 30a, 30 respectively. A resistor 31 is shown in line 30a and a resistor 35 is shown in line 36a.

Referring again to the "span" comparator 34, when the operator attaches a sample of a "span" gas with a known concentration of the toxic gas for which the system has been arranged, and after waiting for the system to become stabilized, the operator may adjust resistor 72 until such time as the "span" signal 38 is energized. Again, if he goes beyond a proper adjustment range, the signal 38 will again be de-energized. The output signal of the "span" comparator will be within a predetermined band around a specific voltage corresponding to the value of the calibration gas, which predetermined specific voltage is determined by resistors 86, 88, 900 connected to operational amplifiers 82, 84.

The signal from adjustment amplifier 24 through line 26 also goes to the fault indicator comparator circuit 40 consisting of an operational amplifier 90 connected through line 93 to a fault indicator relay 44. Relay 44 is normally energized. However, if the output signal from the system goes above a threshhold determined by resistors 92, 94, the relay 44 de-energizes and the output through line 48 to the system controller is blocked.

Thus, as will be appreciated from the above discussion, there is provided, in accordance with this invention, a toxic gas detection system calibrator which may be utilized by anyone untrained in the operation of such systems to re-calibrate on a periodic basis, a toxic gas detection system in order to maintain the system at a proper operating level continuously. Moreover, the system allows the use of only one operator to make the adjustments when required, and the system is arranged to provide a range of adjustments so that an upper and lower limit of the adjustments is provided to enable the operator to make the adjustments within the proper ranges.

While the methods and forms of apparatus herein described constitute preferred embodiments of the invention, it is to be understood that the invention is not limited to these precise methods or forms of apparatus and that changes can be made therein without departing from the scope of the invention which is defined in the appended claims. For example, the remote calibrator is ordinarily arranged to be part of the remote sensing head. However, it will be appreciated, that the calibrator my be incorporated into a "black box" arrangement which can be placed in the system between the remote sensing head and the system controller. Such a positioning will depend upon the conditions under which the system is mounted at a particular site and any limitations that might be prevalent at that particular site. For example, it may be more appropriate for the operator to make the adjustments at a position well away from the remote sensing head because of conditions where the remote sensing head happens to be placed.

What is claimed is:

1. Calibrator apparatus for recalibrating electrochemical gas sensors, comprising
   (a) a housing;
   (b) a source of power;
   (c) an input in said housing for connection to a gas sensor sensing head;
   (d) an output in said housing for connection to a gas sensor controller;
   (e) an adjustment amplifier in said housing;
   (f) first flow communication means extending between said input and said adjustment amplifier;
   (g) second flow communication means extending between said adjustment amplifier and said output;
   (h) said source of power being connected to said first and second flow communication means;
   (i) span adjustment means connected to said adjustment amplifier for adjusting the output of said adjustment amplifier;
   (j) zero adjustment means connected to said adjustment amplifier for adjusting the output of said adjustment amplifier;
   (k) pre-set zero comparator means connected in said second flow communication means for producing a first output signal when the adjusted output of said adjustment amplifier in response to said zero adjustment means lies within first predetermined limits and a second output signal when said adjusted output lies out of said first limits;
   (l) pre-set span comparator means connected in said second flow communications means for producing a first output signal when the adjusted output of said adjustment amplifier in response to said span adjustment means lies within second predetermined limits and a second output signal when said adjusted output lies out of said second limits;
   (m) first indicator means connected to said pre-set zero comparator means for producing a characteristic indication responsive to the production of a said first output signal by said zero comparator means; and (n) second indicator means connected to said pre-set span comparator means for producing a characteristic indication responsive to the production of a said first signal by said span comparator means.

2. The apparatus of claim 1, further characterized by
(a) a differential amplifier in said first flow communication means for converting a dual signal from said input to a single signal to said adjustment amplifier.

3. The apparatus of claim 1 wherein said zero comparator means comprises
(a) a plurality of resistors for establishing said first predetermined limits for said zero adjustment means.

4. The apparatus of claim 1, wherein said span comparator means comprises
(a) a plurality of resistors for establishing said second predetermined limits for said span adjustment means.

5. The apparatus of claim 1 further comprising
(a) pre-set fault comparator means in said second flow communication means for blocking said second flow communication means in response to the adjusted output produced by said adjustment amplifier exceeding a pre-set threshold level.

6. The apparatus of claim 5, further characterized by
(a) a fault indicator relay in said fault comparator means for blocking a signal to said output in response to said pre-set threshhold level.

* * * * *